United States Patent [19]

Mathre et al.

[11] Patent Number: 5,777,105
[45] Date of Patent: Jul. 7, 1998

[54] PROCESS FOR THE PREPARATION OF IMIDAZOLYL MACROLIDE IMMUNOSUPPRESSANTS

[75] Inventors: David J. Mathre, Skillman; Richard F. Shuman, Westfield; Paul Sohar, Warren; Zhiguo Song, Edison, all of N.J.

[73] Assignee: Merck & Co., Inc., Rahway, N.J.

[21] Appl. No.: 649,255

[22] Filed: Jul. 23, 1996

Related U.S. Application Data

[60] Provisional application No. 60/002,726, Aug. 24, 1995.

[51] Int. Cl.$^6$ ............................................. C07D 491/16
[52] U.S. Cl. ................................................... 540/456
[58] Field of Search ...................................... 540/456

[56] References Cited

U.S. PATENT DOCUMENTS

| | | | |
|---|---|---|---|
| 5,247,076 | 9/1993 | Goulet et al. | 540/456 |
| 5,252,732 | 10/1993 | Sinclair et al. | 340/436 |
| 5,344,925 | 9/1994 | Goulet et al. | 540/456 |

FOREIGN PATENT DOCUMENTS

| | | | |
|---|---|---|---|
| 0 365 030 | 4/1990 | European Pat. Off. | C07D 233/90 |

OTHER PUBLICATIONS

Hamamichi, N.; Migasaka, T., Tet. Lett., 26, pp. 4743–4746 (1985).

Nakajima, N.; Horita, K.; Abe, R.; Yonemitsu, O., Tet. Lett., 33, pp. 4139–4142 (1988).

Primary Examiner—Robert T. Bond
Attorney, Agent, or Firm—Mollie M. Yang; David L. Rose

[57] ABSTRACT

Imidazolmethyloxy-substituted tricyclo-macrolide immunosuppressants are prepared by reacting a tricyclo-macrolide with an imidazolmethyl trichloroacetimidate in the presence of an acid. The invention further provides a crystalline salt of imidazolmethyloxy-substituted tricyclo-macrolide, as well as novel compounds useful in the process of the present invention.

7 Claims, 1 Drawing Sheet

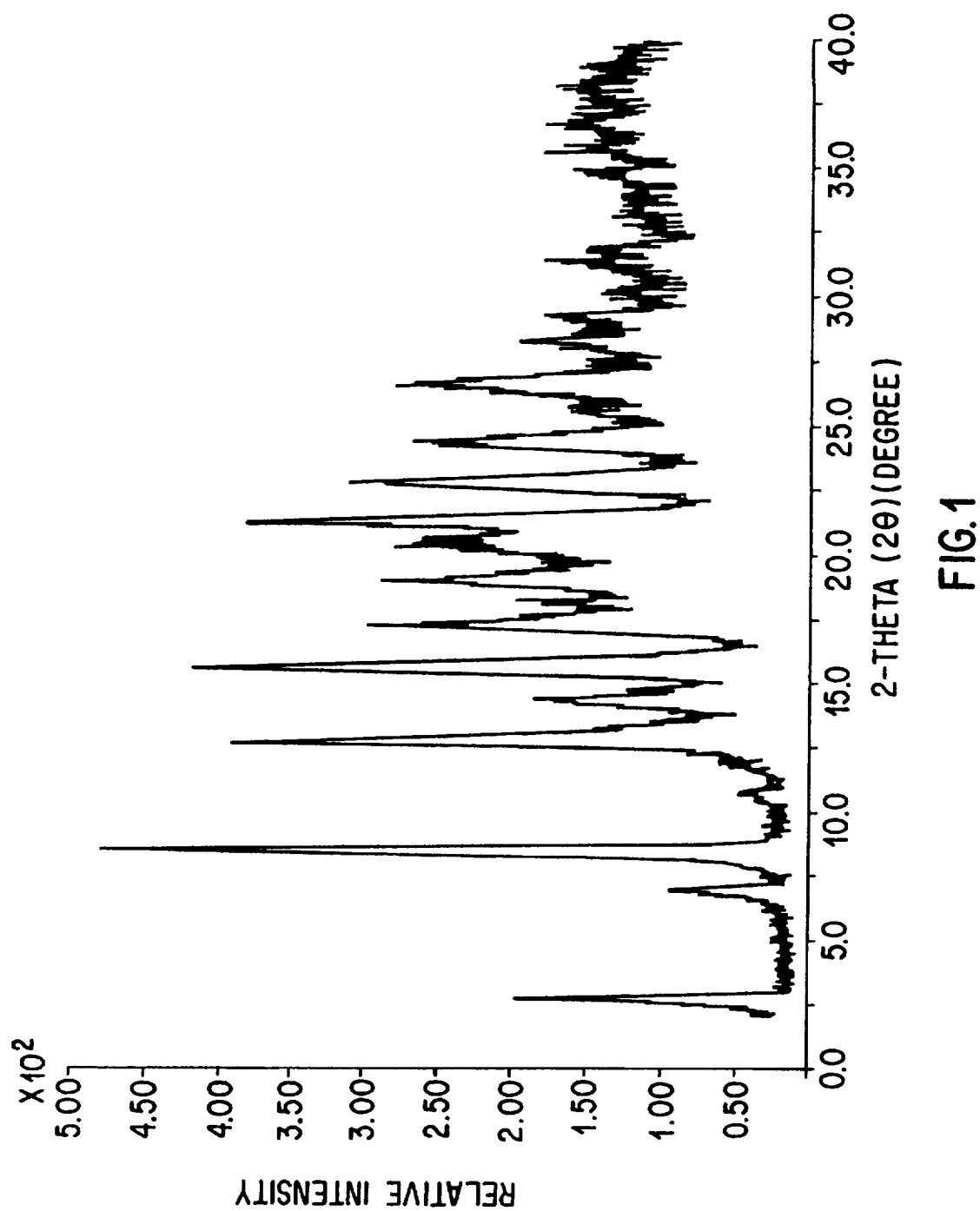

PROCESS FOR THE PREPARATION OF IMIDAZOLYL MACROLIDE IMMUNOSUPPRESSANTS

CROSS REFERENCE TO RELATED APPLICATION

The present application is based on, and claims priority from, provisional application 60/002.726, filed Aug. 24, 1995.

BACKGROUND OF THE INVENTION

The 23-membered tricyclo-macrolide immunosuppressant, tacrolimus, FR-900506, FK-506,

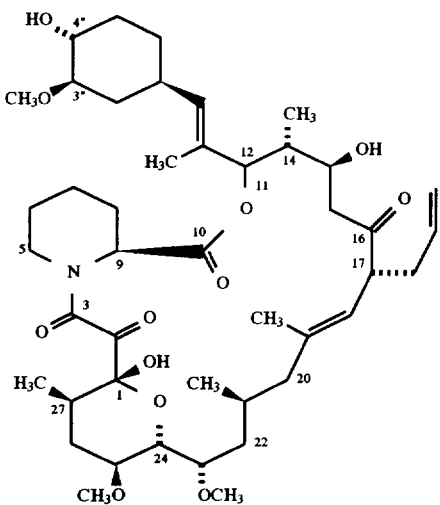

(17-allyl-1.14-dihydroxy-12-[2'-(4"-hydroxy-3"-methoxycyclohexyl)-1'-methylvinyl]-23, 25-dimethoxy-13, 19,21,27-tetramethyl-11,28-dioxa-4-azatricyclo [22.3.1.0$^{4,9}$]-octacos-18-ene-2,3,10,16-tetraone) and related compounds, which were isolated and characterized by Tanaka, Kuroda, and co-workers at Fujisawa Pharmaceutical Co. in Japan, see J. Am. Chem. Soc., 1987, 109, 5031, and U.S. Pat. No. 4,894,366, issued Jan. 16, 1990) have been shown to possess exceptional immuno-suppressive activity. Fujisawa United States patents (U.S. Pat. No. 4,929,611, issued May 29, 1990, U.S. Pat. No. 4,956,352, issued Sep. 11, 1990 and U.S. Pat. No. 5,110,811, issued May 5, 1992) disclose the use of FK-506-type compounds in treating resistance to transplantation. In particular, the compound FR-900506 has been reported to be 100 times more effective than cyclosporin in the suppression of in vitro immune systems (J. Antibiotics 1987, 40, 1256). In addition, these compounds are reputed to possess topical activity in the treatment of inflammatory and hyperproliferative skin diseases and cutaneous manifestations of immunologically-mediated illnesses (EPO Pub. No. 0,315,978).

Many derivatives of FK-506 possessing immunosuppressive activity have since been reported, including those disclosed in U.S. Pat. No. 5,344,925 having an imidazolmethyloxy group at the 4"-position of the FK-506 core structure. In U.S. Pat. No. 5,344,925 the imidazolmethyloxy group is built up via linear synthesis starting from the macrolide FK-506 or a related compound such as FK-520 (in which the 17-allyl group of FK-506 is replaced by an ethyl group). Thus, the free 4"-hydroxyl group on the cyclohexyl ring is elaborated into an ethanaloxy group, which is then reacted with an arylglyoxal and ammonium hydroxide to form aryl-substituted imidazole ring. This process, however, is not practical for large scale preparation of the target product because the overall yield from the expensive macrolide is low, and the macrocyclic intermediates are non-crystalline material requiring several tedious chromatographic purification steps, which are difficult to scale up. Accordingly, there exists a need for a synthetic route to imidazolmethyloxy-substituted FK-506 type compounds that is amenable to scale-up, is economical, and provides the desired product in good yield.

U.S. Pat. No. 5,344,925 also discloses alkylating (or alkenylating or alkynylating) the free hydroxyl group on the cyclohexyl ring using a trichloroacetimidate reagent. The reaction is carried out in methylene chloride/cyclohexane and employs trifluoromethanesulfonic acid as the acid catalyst. This patent does not disclose or teach the use of an imidazolmethyl (or any other heterocycle) trichloroacetimidate to produce the imidazolmethyloxy compounds.

Although the generic disclosure of U.S. Pat. No. 5,344,925 encompasses pharmaceutically acceptable salts of the imidazolmethyloxy macrolides, and the tartrate is one of the many possible salts enumerated, the only example of a salt of the compounds claimed therein is that of a hydrochloride salt; furthermore, there is no indication that the exemplified hydrochloride salts of several compounds are crystalline.

SUMMARY OF THE INVENTION

The present invention provides a novel and efficient process for the preparation of imidazolmethyloxy-substituted macrolide immunosuppressants, which comprises the reaction of an imidazolmethyloxy trichloroacetimidate with the macrolide in the presence of an acid to form the ether bond. Also provided in the present invention are crystalline tartrate salt of the imidazolmethyloxy-substituted macrolide, as well as the imidazolmethyloxy trichloroacetimidate used in the process.

BRIEF DESCRIPTION OF THE DRAWINGS

FIG. 1 shows the X-ray powder diffraction pattern of the tartrate salt of the compound of formula I. The X-ray powder diffraction pattern was generated on a Philips APD1700 (Automated Powder Diffractometer) using copper radiation.

DETAILED DESCRIPTION OF THE INVENTION

The present invention provides a process for the preparation of the compound of formula I:

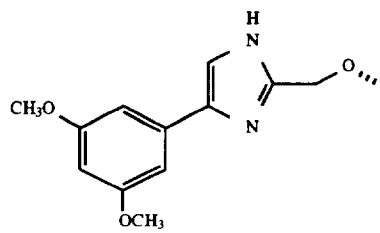

-continued

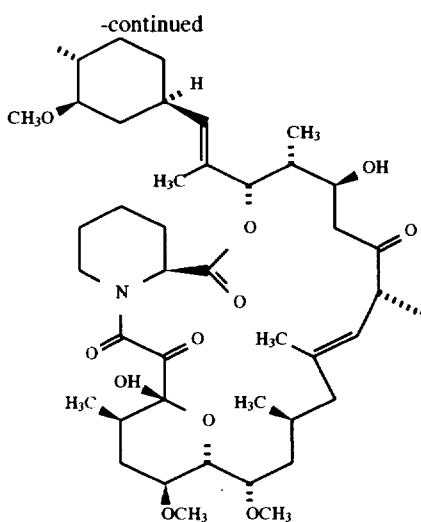

which comprises
(1) reacting the compound of formula II:

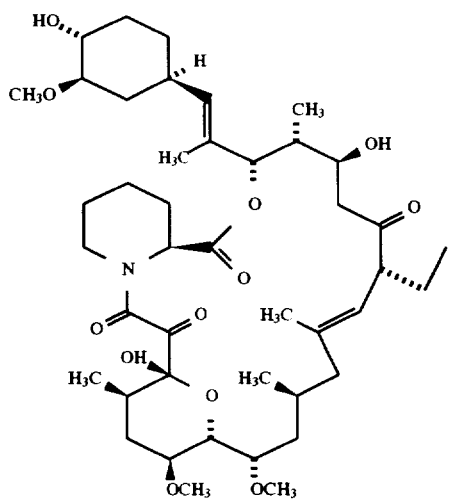

with a compound of the formula III:

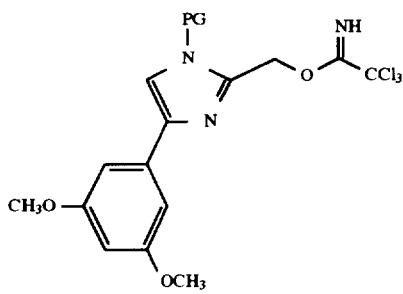

in an inert organic solvent comprising acetonitrile, and an amide of the formula $R^1CONR^2R^3$ or a carbamate of the formula $R^1OCONR^2R^3$; and in the presence of an acid; wherein PG is an imidazole protecting group, $R^1$, $R^2$ and $R^3$ are independently hydrogen or $C_{1-7}$ alkyl, or $R^1$ an $R^2$ together form $-(CH_2)_{2-3}$; and (2) removing the imidazole protecting group.

In a preferred embodiment, the process further comprises: treating the compound of formula I in its free base form with L-tartaric acid; and isolating the crystalline tartrate salt of the compound of formula I.

In another preferred embodiment, the solvent comprises acetonitrile and an amide, wherein the amide is selected from N,N-dimethylpivalamide and N,N,2-trimethylpropanamide.

In another preferred embodiment, the acid is selected from tetrafluoroboric acid and trifluoromethanesulfonic acid.

In yet another preferred embodiment, the imidazole protecting group, PG, is selected from tetrahydrofuranyl, tetrahydropyranyl, and 2-methyltetrahydrofuranyl. More preferably, PG is tetrahydrofuranyl.

The present invention provides in another aspect the crystalline tartrate salt of the compound of formula I.

In yet another aspect, the present invention provides the trichloroacetimidate of formula III, which is useful in the synthesis of the immunosuppressant of formula I. In a preferred embodiment, the PG of the trichloroacetimidate of formula III is tetrahydrofuranyl.

As used herein, the term "alkyl" includes those alkyl groups of a designated number of carbon atoms of either a straight, branched, or cyclic configuration. Examples of "alky" include methyl, ethyl, propyl, isopropyl, butyl, sec- and tert-butyl, pentyl, hexyl, heptyl, cyclopropyl, cyclobutyl, cyclopentyl, cyclohexyl, cycloheptyl, norbornyl, and the like.

"Imidazole protecting group" may be any group conventionally used to protect imidazole, and whose introduction and removal does not substantially affect the integrity of the rest of the molecule, or substantially interfere with any of the subsequent reactions to be carried out. Suitable imidazole protecting groups include amino acetal derivatives such as methoxymethyl, 1-ethoxyethyl, trimethylsilylethoxymethyl, tetrahydropyranyl, tetrahydrofuranyl, 2-methyltetrahydrofuranyl, dimethylorthoformate, and the like.

In the process of the present invention, the tricyclomacrolide starting material of formula II is well known in the art. The preparation of FK-506 and related compounds, e.g. FK-520 (17-ethyl-1,14-dihydroxy-12-|2'-(4"-hydroxy-3"-methoxycyclohexyl)-1'-methyl-vinyl|-23,25-dimethoxy-13,19,21,27-tetramethyl-11,28-dioxa-4-azatricyclo |22.3.1.0$^{4,9}$|octacos-18-ene-2,3,10,16-tetraone), are described in for example, U.S. Pat. No. 4,894,366, issued Jan. 16, 1990, EPO Publication No. 0,184,162, J. Am. Chem. Soc., 1987, 109, 5031 and J. Antibiotics, 1987, 40, 1249.

The trichloroacetimidate starting material of formula III may be prepared according to the reaction sequence shown in Scheme I.

SCHEME I

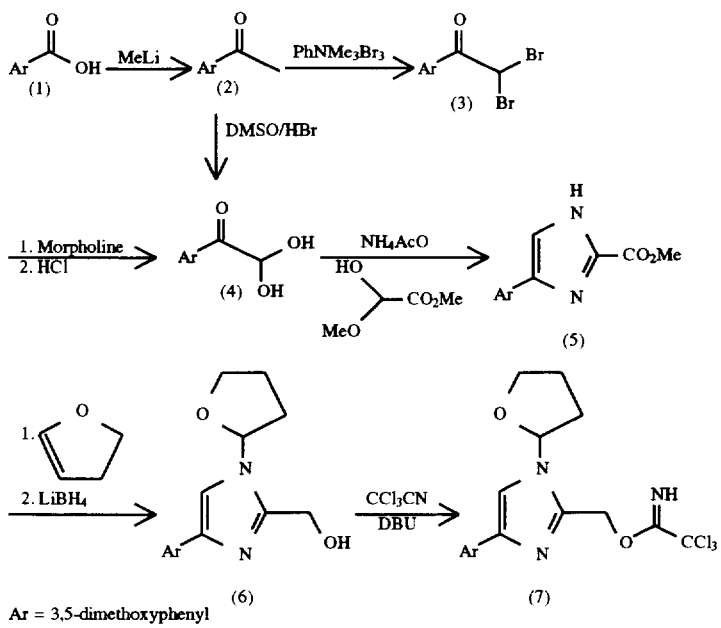

Ar = 3,5-dimethoxyphenyl

Thus, 3,5-dimethoxybenzoic acid (1) is first converted to the corresponding acetophenone (2) using methyllithium in an inert organic solvent such as tetrahydrofuran, methyl t-butyl ether and the like. The acetophenone (2) is then treated with phenyltrimethylammonium tribromide in an ether solvent such as dimethoxy ethane to provide the dibromoacetophenone (3). Reaction of the dibromoacetophenone (3) with morpholine at an elevated temperature, for example from about 50 ° to about 55° C., followed by hydrolysis with aqueous HCl gives the phenylglyoxal (4), which crystallizes as the monohydrate from water/acetonitrile. Alternatively, (4) may be prepared from (2) directly by treating (2) with dimethylsulfoxide and HBr at a temperature of between about 50° to about 90° C. The reaction of (4), ammonium acetate and methyl glyoxylate hemiacetal in acetonitrile provides the imidazole (5). The tetrahydrofuranyl protecting group is introduced with dihydrofuran and a catalytic amount of p-toluenesulfonic acid. Reduction of the protected imidazole ester to the primary alcohol using lithium borohydride produces the protected imidazole alcohol (6), which is then converted to the trichloroacetimidate (7) using trichloroacetonitrile and 1,8-diazobicyclo[5.4.0]undec-7-ene.

A person skilled in the art will appreciate that the reaction sequence shown in Scheme I is illustrative only. Reagents other than those specifically named may be used; in particular, the scheme depicts tetrahydrofuranyl as the imidazole protecting group, other suitable protecting group may be used and a person skilled in the art will be able to select and introduce the protecting group without undue experimentation. For example tetrahydropyranyl may be introduced with 3,4-dihydro-2H-pyran, 2-methyltetrahydrofuranyl may be introduced with 2-methyl-4,5-dihydrofuran.

The process of the present invention involves the coupling of a macrocycle of formula II with a trichloroacetimidate of formula III to produce an imidazolyl substituted macrocycle of formula I, as shown in Scheme II.

SCHEME II

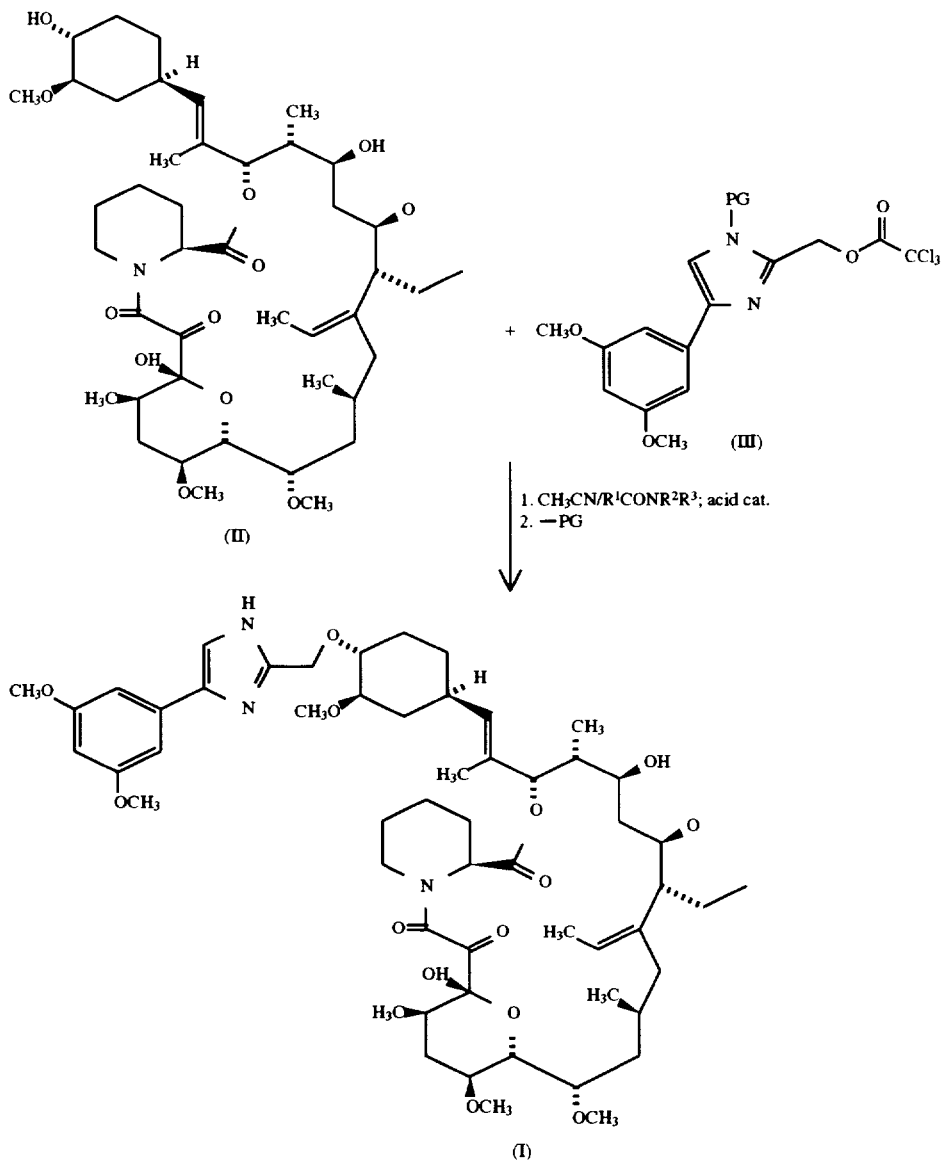

The coupling reaction is carried out in inert organic solvent and in the presence of an acid catalyst. Suitable solvents include, but are not limited to, ethers such as dimethyl ether, diethyl ether, tetrahydrofuran; halogenated alkanes such as methylene chloride, 1,2-dichloroethane; nitriles such as acetonitrile, propionitrile; nitroalkanes such as nitromethane and nitroethane; amides such as dimethylformamide, dimethylispropylamide, dimethylpivalamide, methylpyrrolidinone, dimethylbenzamide; and carbamates such as 3-methyl-2-oxazolidinone, and methyl N,N-dimethylcarbamate. The solvent system used in the reaction may be a single solvent or a combination of 2 or more solvents. Preferably, acetonitrile and an amide or a carbamate is used in combination. The ratio of acetonitrile:amide may range from about 1:1 to about 20:1. The preferred solvent combination is acetonitrile and N,N-dimethylpivalamide or N,N,2-trimethylpropionamide; more preferably acetonitrile and N,N-dimethylpivalamide is used. Suitable acid may be a Lewis acid such as boron trilluoride, or a protonic acid such as a sulfonic acid or tetrafluoroboric acid. Preferably, a strong protonic acid such as triflic acid or tetrafluoroboric acid is used.

The reaction is conducted at a temperature below about 0° C., typically at about -30° to about -5° C. for about 1 to 3 hours, to provide the imidazole protected ether macrolide. The imidazole protecting group may be removed using methods well known in the art; for example, when the protecting group is tetrahydrofuranyl, it can be removed with an acid in an alcohol or water as solvent. The desired final product in free base form may be purified using chromatographic techniques, such as silica gel column chromatography.

As another means of purifying the compound of formula I, attempts had been made to crystallize, without success, the free base form from a variety of solvent systems such as hexane, diethyl ether, ethyl acetate, tetrahydrofuran and acetone. The free base has been converted to a variety of salts, for example, chloride, sulfite, bisulfate, phosphate, mesylate, tosylate, maleate, etc; however, none of the salts could be obtained as crystalline material. Thus, it is surprising that when the free base of a compound of formula I in ethyl acetate is treated with an aqueous solution of L-tartaric acid, crystalline L-tartrate salt of the compound of formula I is obtained. The crystalline tartrate salt is in the form of fine needles, and its X-ray powder diffraction pattern is as shown in FIG. 1.

The crystalline tartrate salt provides a facile means for the purification of a compound of formula I. Furthermore, it is particularly suited for use in pharmaceutical formulation.

The utility and methods of using a compound of formula I and its pharmaceutically acceptable salt are fully described in U.S. Pat. No. 5,344,925, which is hereby incorporated by reference.

The tartrate salt of the compound of Formula I can be used in the form of a pharmaceutical preparation, for example, in solid, semisolid or liquid form, in admixture with an organic or inorganic carrier or excipient suitable for external, enteral or parenteral applications. The active ingredient may be compounded, for example, with the usual nontoxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. For example, the compounds of Formula I may be utilized with hydroxypropyl methylcellulose essentially as described in U.S. Pat. No. 4,916,138, issued Apr. 10, 1990, or with a surfactant essentially as described in EPO Publication 0,428,169. Oral dosage forms may be prepared essentially as described by T. Hondo, et al., *Transplantation Proceedings*, 1987, XIX, Supp. 6, 17–22. Dosage forms for external application may be prepared essentially as described in *EPO Publication* 0,423,714. The active object compound is included in the pharmaceutical composition in an amount sufficient to produce the desired effect upon the process or condition of diseases.

In practical use, the tartrate salt of the compound of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations including liquids for soft gelatin capsule fill, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablet.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 500 mg of the active ingredient and each cachet or capsule contains from about 1 to about 500 mg of the active ingredient.

The amount of active ingredient that may be combined with the carrier materials to produce a single dosage form will vary depending upon the host treated and the particular mode of administration. For example, a formulation intended for the oral administration of humans may contain from 0.5 mg to 5 gm of active agent compounded with an appropriate and convenient amount of carrier material which may vary from about 5 to about 95 percent of the total composition. Dosage unit forms will generally comprise from about 0.01 mg to about 500 mg, and preferably about 0.5 mg to about 100 mg of active ingredient. For external administration the compound of Formula I may be formulated within the range of, for example, 0.0001% to 60% by weight, preferably from 0.001 to 10% by weight, and most preferably from about 0.005 to 0.8% by weight.

The following abbreviations are used in the experimental procedures provided hereinbelow:

DBU=1,8-diazobicyclo[5.4.0]undec-7-ene
DME=dimethoxyethane
DMSO=dimethylsulfoxide
MeCN=acetonitrile
MTBE=methyl t-butyl ether
PTT=phenyltrimethylammonium tribromide
THF=tetrahydrofuran

PREPARATION I

3',5'-Dimethoxyacetophenone

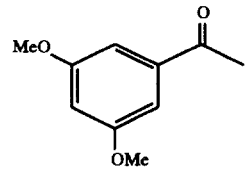

To a three-neck round bottom flask equipped with a mechanical stirrer, a nitrogen inlet and a thermometer was charged MTBE (60 mL, KF≦50 mcg/ml) and 3',5'-dimethoxybenzoic acid (10.92 g, 60 mmol) under nitrogen. The slurry resulted was then cooled to -30° C. and 1.08M methyllithium in 4/1 THF/cumene (109 mL, 107.7 mmol) was added slowly while keeping the temperature of the reaction at -30°—20° C. The slurry became thinner as the methyllithium was added. The reaction mixture was allowed to warm to -5° C. over 2 hrs. Then it was aged at room temperature for one hour.

To quench the reaction, the suspension was added dropwise to a flask charged with 1.0N HCl (144 mL) and vigorously stirred. The reaction temperature was controlled at ≦0° C. The reaction vessel was rinsed with 2×15 mL MTBE. The pH of the aqueous layer at the end was 6. The layers were then separated and the organic layer washed with 120 mL saturated sodium bicarbonate, 2×120 mL water. The organic layer was dried with sodium sulfate which was removed by filtration and washed with 3×25 mL MTBE. The solution was concentrated under vacuum to a minimum volume and flushed with 2×10 mL MTBE, 2×10 mL heptane to an yellow oil, wt 11.0 g.

A portion of this product, 8.98 g was stirred together with 45 mL heptane overnight and then at −10°—15° C. for 1 hr. The crystalline solid was collected by filtartion and washed with ice-chilled 5 mL hepatne. It was air dried, wt. 7.6 g (84% yield), amber solid. $^1$H NMR and $^{13}$C NMR confirm the structure compared with authentic samples.

PREPARATION II 2,2-Dibromo-3',5'-dimethoxyacetophenone

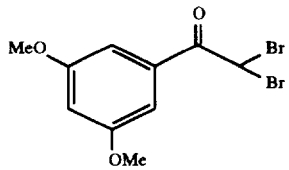

To a round bottom flask equipped with a mechanical stirrer, a temperature probe was added DME (53 L), 3',5'-dimethoxyacetophenone (4.215 kg, 23.4 mol). After all the ketone was dissolved, PTT (18.47 kg, 49.12 mol) was added over 30 min. Temperature of the reaction rose from 23° to 30° C. A white solid precipitated out. The temperature of the reaction mixture dropped slowly over 5 hours to 25° C.

This mixture was stirred overnight (~22 hrs), filtered to remove the solid side product and the solid was washed with 56 L MTBE. The brown colored filtrate was transferred to a vessel charged with a premixed solution containing 36 L of brine and 10 L of 0.5M sodium sulfite (freshly prepared). It was then washed with 36L of brine. The organic layer was then concentrated in vacuo to a minimum volume, flushed with 10 L of acetonitrile and then 10 L MTBE and then 10 L heptane. During the flushing, the temperature of the batch was kept above 35° C. Then heptane was added to the residue to a total volume of 34 L (ca. 28 L heptane) and the mixture stirred vigrously over night. A dense crystalline solid was formed. The solid was colletecd by filtration and washed with 3×2 L heptane and dried under sweeping nitrogen to 6.59 kg (83%) of the title compound as a tan solid.

A pure sample was prepared by dissolving the crude product in MTBE and filtering the solution through silica gel and then crystallizing from MTBE-hexane mixture. The compound is a white solid, m.p.=72°–73° C. $^1$H NMR (CDCl$_3$)δ7.17 (2H, d, J=2.3 Hz), 6.69–6.70 (2H, m), 3.89 (s, 6H). $^{13}$C NMR (CDCl$_3$)δ185.8, 160.9, 132.5, 107.3, 106.7, 55.7, 39.6. CIMS MH$^+$=337.

Analysis Calcd. for C$_{10}$H$_{10}$Br$_2$O$_3$ C 35.54, H 2.98, Br 47.28 Found C 35.51, H 2.81, Br 47.17.

PREPARATION III

3',5'-Dimethoxyphenylglyoxal monohydrate

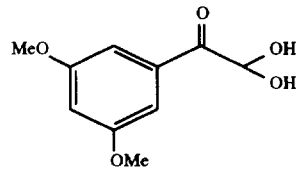

To a three-neck round bottom flask equipped with a mechanic stirrer and a temperature probe was added morpholine (3.67 ml, 42 mmol) and acetonitrile (5.1 ml). To this solution was added 2,2-dibromo-3',5'-dimethoxyacetophenone (3.4 g, 10 mmol) in several portions while the heat generated in the reaction kept the temperature around 50° C. After all the dibromide solid was added, thick slurry was heated to 50°–55° C. for one hour.

After one hour, the reaction mixture was cooled to 0° C. and 7.7 mL 3N HCl was added in several portions while keeping the reaction temperature below 20° C. The color of the solution turned dark brown and then to very light amber. Then 23 ml water was added during which massive white solid precipitated out. The mixture was cooled to 0° C. for 1 hour before it was filtered. The solid was washed with 3×3 ml water, dried with sweeping air, wt 1.72 g (81% yield), off-white color. m.p.≧95° C. (dec.). Two kinds of crystals forms were observed by x-ray. $^1$H NMR (CD$_3$CN) δ7.19 (d, J=2.3 Hz, 2H), 6.76 (t, J=2.3 Hz, 1H), 5.83 (t, J=8.4 Hz, 1H), 4.80 (d, J=8.4 Hz, 2H), 3.82 (s, 6H). $^{13}$C NMR (CD$_3$CN) 196.4, 162.0, 136.2, 108.0, 106.8, 88.1, 56.3. CIMS MH$^+$—H$_2$O=195

Analysis Calcd. for C$_{10}$H$_{12}$O$_5$ C 56.60, H 5.70 Found C 56.61, H 5.83

PREPARATION IIIa

3',5'-Dimethoxyphenylglyoxal dihydrate.

3',5'-Dimethoxyacetophenone (4.5 g, 25 mmol) was dissolved in DMSO (37.5 ml), and heated to 87° C. with an N$_2$ sweep. To this solution was added HBr (48%, 2.5 ml, 22 mmol). The internal temperature rose to 94° C., then slowly to 101° C.

The batch temperature was maintained at 90° C. for 45 minutes. The reaction was quenched with water (125 ml) and the internal temperature was adjusted to 60° C. (from 40° C.). To the mixture was added soka floc (4.5 gm) and the batch was stirred at 60° C. for 5 minutes. The batch was filtered and the cake was washed with 60° C. water (25 ml).

The batch was cooled to 23° C., then to 0° C., and aged at 0° C. for 1h and filtered. The flask and cake were rinsed with ice-cold H$_2$O (40 ml). The product was air dried with suction for 18h to afford the title compound (4.1 gm) as an off white solid which was 96.6% pure by weight (74% yield). The isolated solid was 98A% pure by HPLC analysis (HPLC conditions: 50:50:0.1 to 80:20:0.1 acetonitrile:water:phosphoric acid in 20 minutes, flow=1.5 ml/min, UV detection at 220 nm, Zorbax Phenyl at 30° C. Starting material 'R=3.2 minutes, product tR=2.2 minutes, DMSO tR=1.78 minutes). A 1.25 gm sample was dissolved in 25 ml of dry acetonitrile (KF=100). The KF of the resulting solution was 2.05 mg of water in a 250 µl sample (ie. 12.5 mg of solid). This corresponds to 16.4% water, or a dihydrate of the title compound.

13

PREPARATION IV

2-Carbomethoxy-4(5)-(3'5'-dimethoxyphenyl) imidazole

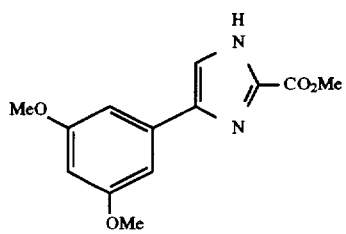

To a three-neck round bottom flask equipped with a mechanical stirrer and an addition funnel was added water (10 mL), ammounium acetate(1 1.55 g, 150 mmol), acetonitrile (50 ml). To the addition funnel was added a solution of the glyoxal monohydrate of PREPARATION III (10.6 g, 50 mmol) and methyl 2-hydroxy-2-methoxyacetate (18 g) in acetonitrile (195 mL) and water (5 ml). Then methyl 2-hydroxy-2-methoxyacetate (6 g) was added to the reaction flask immediately followed by dropwise addition of the glyoxal solution over 10–15 min while the reaction mixture was vigorously stirred. Additional 5 ml acetonitrile was used for rinse.

The reaction mixture was stirred for 1 hr and was concentrated in vacuo to a minimum volume and flushed with 50 mL of ethyl acetate. The residue was mixed with 200 mL of ethyl acetate and 200 mL water, transferred to a separatory funnel and the two layers separated. The top organic layer was washed with 2×100 mL of saturated sodium bicarbonate (caution: gas evolution) and then 2×100 mL of water.

The top organic layer was concentrated in vacuo to a minimum volume (~20 ml) and flushed with 20 ml ethyl acetate. This residue was then dissolved in 100 ml ethyl acetate and seeded. Then 100 mL hexane was added and the mixture stirred overnight. The solid was collected by filtration and washed with 2×10 mL 2/1 hexane/ethyl acetate. It was dried by sweeping air, wt. 8.4 g (65% yield), off-white crystals. HPLC showed 97% area. A sample for analysis was prepared by recrystallization from a 2:1 mixture of ethyl acetate/ hexanes. mp 154°–155° C. $^1$H NMR (CDCl$_3$) δ7.49 (s, 1H), 6.93 (s, 2H), 6.44 (t, J=2.2 Hz, 1H), 4.01 (s, 3H), 3.85 (s, 3H). $^{13}$C NMR (CDCl$_3$+CH$_3$COOH) 161.1, 159.9, 139.9, 136.9, 132.2, 122.2, 103.4, 100.7, 44.4, 53.0. CIMS MH$^+$=305

Analysis Calcd. for C$_{13}$H$_{14}$N$_2$O$_4$ C 59.54, H 5.38, N 10.68
Found C 59.37, H 5.15, N 10.58

14

PREPARATION V 1-(2'-Tetrahydrofuranyl)-2-carbomethoxy-4-(3",5"-dimethoxyphenyl) imidazole

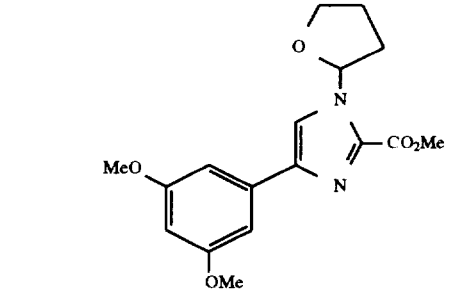

To a round bottom flask charged with anhydrous THF (20 mL) and 2-carbomethoxy-4(5)-(3',5'-dimethoxyphenyl) imidazole (1.05 g, 4.0 mmol) was added 3,4-dihydrofuran (0.56 g, 8.0 mmol). The solution was heated to 50° C. in a oil bath and p-toluenesufonic acid monohydrate (20 mg, 0.1 mmol) was added. The reaction mixture was stirred at 50° C. for 60 min.

After one hour, the solution was cooled to room temperature. This crude product solution was used directly for the next step without purification. Otherwise, it can be isolated after workup with ethyl acetate and sodium carbonate solution and crystallization from 1/1 ethyl acetate-hexane mixture in 82% yield. The product is a white solid, m.p.= 194°–196° C. $^1$H NMR (CDCl$_3$) δ7.53 (s, 1H), 6.97 (d, J=2.3 Hz, 2H), 6.69 (dd, J=2.2 Hz, 6.4 Hz) 6.4 (t, J=2.3 Hz, 1H), 4.30–4.40 (m, 1H), 4.05–4.10 (m, 1H), 3.97 (s, 3H), 3.84 (s, 3H), 2.50–2.65 (m, 1H), 1.9–2.2 (m, 3H). $^{13}$C NMR (CDCl$_3$) δ161.0, 159.6, 141.8, 135.0, 134.5, 117.6, 103.3, 100.1, 89.0, 70.36, 55.5, 52.5, 35.2, 23.5. CIMS MH$^+$=333
Analysis Calcd. for C$_{17}$H$_{20}$N$_2$O$_5$ C 61.44, H 6.07, N 8.43
Found C 61.29, H 6.00, N 8.20

PREPARATION VI 1-(2'-Tetrahydroiuranyl)-2-hydroxymethyl-4-(3",5"-dimethoxyphenyl) imidazole The product solution from PREPARATION V (ca. 1.32 g, ca. 4.0 mmol) was cooled to 0° C. under nitrogen. To this reaction mixture (cloudy) was added methanol (256 mg, 4.0 mmol), and lithium borohydride (176 mg, 8.0 mmol). This mixture was stirred at 0° C. for 15 min then was allowed to warm to room temperature.

After 45 min, the mixture was cooled to 0° C. Then 12 ml saturated ammonium chloride solution, 8 mL water were added. This mixture was transferred to a separatory funnel and mixed with 40 mL ethyl acetate. The two layers were separated and the top organic layer was washed with 20 mL water. The organic layer was concentrated in vacuum to an oil residue and flushed with 10 ml THF, 2×10 ml ethyl acetate. A sample was taken from this residue. $^1$H NMR confirmed the structure. This crude product was used directly for the next step or it can be isolated by crystallization from 1/1 THF-hexanes mixture as white solid in 68% for the two steps from the unprotected imidazole. m.p.= 109°–111° C. $^1$H NMR (CDCl$_3$) δ7.13 (s, 1H), 6.85 (d, J=2.3 Hz, 2H), 6.36 (t, J=2.3 Hz, 1H), 6.08 (dd, J=2.8, 6.4 Hz, 1H), 5.05 (br.s, 1H), 4.77 (ABq, J=3.6 Hz, Δυ=7.9 Hz, 2H), 4.05–4.15 (m, 1H), 3.90–4.00 (m, 1H), 3.83 (s, 6H), 2.2–2.4 (m, 1H), 2.0–2.2 (m, 3H). $^{13}$C NMR (CDCl$_3$) δ161.0, 147.4, 139.8, 135.6, 112.7, 102.82, 99.4, 85.6, 69.0, 56.8, 55.4, 32.6, 24.5. CIMS MH+=305.

Analysis Calcd. for C₁₃H₁₄N₂O₄ C 59.54, H 5.38, N 10.68 Found C 59.37, H 5.15, N 10.58

PREPARATION VII 1-(2'-Tetrahydrofuranyl)-2-trichloroacetimidoxymethyl-4-(3",5"-dimethoxyphenyl)imidazole

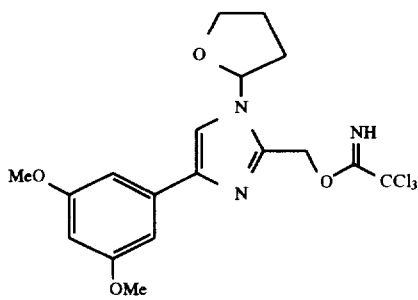

The crude product from PREPARATION VI (ca. 1.2 g, ca. 4.0 mmol) was dissolved in dry ethyl acetate (15 mL) and was then cooled to 0° C. and trichloroacetonitrile (0.864 g, 6.0 mmol) and DBU (20 μL, 0.066 mmol) were added. This mixture was stirred at 0° C. over 45 min. White solid precipitated out.

After 45 min, the reaction mixture was allowed to warm to room temperature and 45 mL ethyl acetate was added. This hazy mixture was filtered through a pad of celite (pre-washed with ethyl acetate) and the celite was washed with 3×4 mL ethyl acetate. The Kf of the filtrate was 750 mcg/mL. It was dried azeotropically by removing ethyl acetate under vacuum (27" vacuum, 40° C. bath temp.). Ethyl acetate was added and removed in 20 mL portions. A total of 100 mL ethyl acetate was used to obtain a Kf of 250 mcg/mL for the product solution at ~40 mL volume. An additional 20 mL ethyl acetate was added and the solution was concentrated to 10 g (~10 mL solvent and ~2 g product). Then at room temperature, 15 mL hexane was added. A thick white slurry resulted. After 30 min, the solid was collected by filtration and washed with 2 mL 2/1 hexanes/THF, 2×2 mL hexanes. It was dried with sweeping nitrogen, wt. 1.50 g (79% for the three steps from the unprotected ester). m.p=148°–150° C.

Part of the above product, 1.43 g, was dissolved in 60 mL anhydrous ethyl acetate (Kf≦150 mcg/mL). The solution was concentrated to near dryness on a rotavaporator (27" vacuum, 40° C. bath temp.). The last portion of the solvent was removed with a vacuum pump at room temperature. A white solid resulted, wt. 1.42 g (79% for the three steps from the unprotected ester). Kf=200–400 mcg/mL. ¹H NMR (CDCl₃) δ8.54 (s, 1H), 7.32 (s, 1H), 6.94 (d, J=2.2 Hz, 2H), 6.38 (t, J=2.0 Hz, 1H), 6.10 (dd, J=2.6, 6.2 Hz, 1H)5.46 (s, 2H), 4.15–4.25 (m, 1H), 3.95–4.05 (m, 1H), 3.84 (s, 6H), 2.35–2.55 (m, 1H), 2.05–2.30 (m, 3H). ¹³H NMR (CDCl₃) d 161.9, 161.0, 141.1, 135.8, 113.7, 102.8, 99.7, 90.9, 86.0, 69.2, 63.3, 55.4, 33.5, 24.5. CIMS MH+=448.

Analysis Calcd. for C₁₈H₂₀Cl₃N₃O₄ C 48.18, H 4.49, N 9.36 Cl 23.70 Found C 48.09, H 4.37, N 9.43, Cl 24.10

The following examples are provided to more fully illustrate the claimed invention, and are not to be construed as limiting the scope of the invention in any manner.

EXAMPLE 1

17-Ethyl-1,14-dihydroxy-12-|2'-(4"-(4'"-(3"".5""-dimethoxyphenyl)-2'"-imidazolylmethyloxy)-3"-methoxycyclohexyl)-1'-methylvinyl|-23,25-dimethoxy-13, 19,21,27-tetramethyl-11,28-dioxa-4-azatricyclo-|22.3.1.0⁴,⁹|octacos-18-ene-2,3,10,16-tetraone

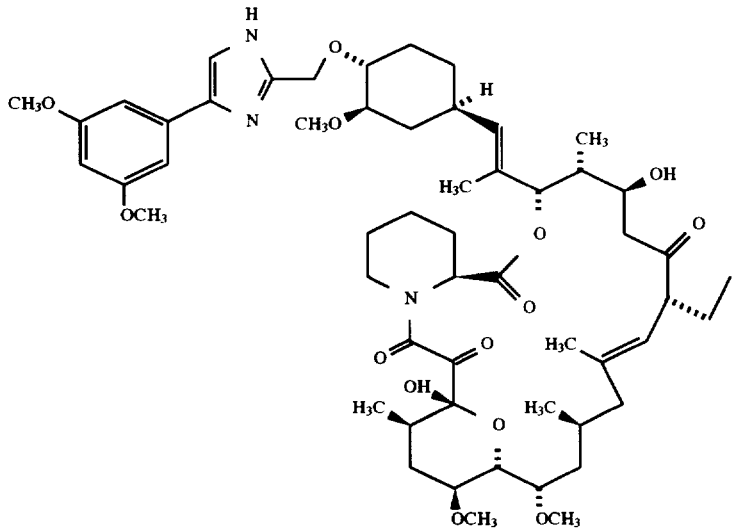

To a 50L five-neck flask charged with 1-(1'-tetrahydrofuranyl)-2-trichloroacetimidoxymethyl-4-(3",5"-dimethoxyphenyl) imidazole (Kf=900 mcg/g, 640 g, 1.42 mol) and equipped with a temperature probe, a stirrer and a nitrogen inlet was added acetonitrile (8.25 L), N,N-dimethyl pivalamide (8.25 L) and FK-520 (pre-dried in 50° C. vacuum oven overnight to Kf≦1 000 mcg/g, 2.00 kg 2.51 mol). After all of the solids were dissolved, the reaction mixture was cooled to −25° C. Tetrafluoroboric acid etherate (338 mL, 2.07 mol) was charged via a dry addition funnel. The reaction temperature changed from −26° to 20° C. The reaction mixture was allowed to warm to −7° C. over two hours. Then water (12.4 L) was added and the mixture was heated to 50° C. for 24 hours. HPLC assay at 22 hrs indicated ~97% deprotection.

The mixture was cooled to room temperature and transferred to a separation vessel and mixed with 34 L ethyl acetate, 12 L saturated sodium bicarbonate. The two layers were separated and the organic layer was washed with 10 L brine. The combined aqueous layer was extracted with 10 L ethyl acetate. The combined organic layer was concentrated in vacuum to a minimum volume (~10 L) and flushed with 5 L acetonitrile. The residue was transferred to a separation vessel, mixed with 16 L acetonilrile and extracted with 5×36 L hexanes. The desired title compound stayed in the bottom acetonitrile layer. The acetonitrile layer was concentrated in vacuum to a minimum volume and flushed with 2.5 L ethyl acetate to a thick brown oil. wt 5.125 kg. HPLC indicated 845 g of the title compound.

EXAMPLE 1A

Alternative Preparation of Compound of Example 1

To a 72L round bottom flask was charged 1.3 kg of 1-(1'-tetrahydrofuranyl)-2-trichloroacetimidoxymethyl-4-(3",5"-dimethoxyphenyl) imidazole, 3.448 kg of FK-520 and 19.5 L of N,N-dimethyl trimethylacetamide. The Kf was 2400 mcg/ml for the solution. It was dried by adding 10 L of acetonitrile (Kf=100 mcg/ml) and removing it under vacuum at 15°-25° C./29" Hg (Kf=380 mcg/ml). The solvent flush with $CH_3CN$ was repeated twice (final Kf=50mcg/ml). The reaction mixture was diluted with $CH_3CN$ (6.5 L) and cooled to $-33°$ C. under $N_2$. Then 522 gm of trifluoromethanesulfonic acid was charged into the batch. The reaction temperature was warmed to 0° C. over 3 hours. Then 6.5 L of water was added and the pH of the reaction mixture was adjusted with tifluromethanesulfonic acid to ~2–3 if it is higher. The mixture was heated to 50° C. for 24 hours. The mixture was cooled to room temperature and mixed with 13 L of ethyl acetate and 6.5 L of saturated sodium bicarbonate. The two layers were separated and the organic layer was washed with 6.5 L of brine. The combined aqueous layer was extracted with 6.5 L of ethyl acetate. The combined organic layer was concentrated in vacuo to a minimum volume and flushed with 12 L of acetonitrile (the residue had a Kf=7% water). The residue was flushed with isopropanol (15L and 5L, to a Kf=0.37%). The residue was then flushed with 10 L of acetonitrile, diluted with 40 L of acetonitrile and extracted with 4×80 L of hexane. The desired title compound stayed in the lower acetonitrile layer and the dimethyl pivalamide was extracted into the hexane layer. The acetonitrile layer was concentrated in vacuo to a minimum volume as a thick brown oil; wt=12.844 kg. HPLC analysis showed this to be 12.5% pure by weight. The yield of the title compound was 1.60 kg (55% based on the side chain and 36% based on FK-520).

EXAMPLE 2

Purification of 17-Ethyl-1,14-dihydroxy-12-[2'-(4"-(4'''-(3"",5""-dimethoxyphenyl)-2'''-imidazolylmethyloxy)-3"-methoxycyclohexyl)-1'-methylvinyl]-23,25-dimethoxy-13, 19,21,27-tetramethyl-11,28-dioxa-4-azatricyclo-[22.3.1 .0$^{4,9}$]octacos-18-ene-2,3,10,16-tetraone by silica gel chromatography The crude title compound obtained from the procedure of Example 1 using 1.0 g imidazole trichloroacetimidate side chain and 2.6 g of FK-520 was purified using column chromatography.

Silica gel 60A (200 g, E. Merck, 240–400 mesh) was slurry packed with 600 ml 1:1 ethyl acetate and heptane and washed with 200 ml more of the same solvent. The packed volume was 1.5"×14" in size (3.8 cm diameter and 35.5 cm long) and about 400 ml.

The product mixture solution that was from the reaction of 1.0 g imidazole trichloroacetimidate side chain with 2.6 g FK-520 (14 mL, containing about 1.2 g of title compound) was loaded to the silica gel column. The container was rinsed with 5 ml more of 1/1 ethyl acetate/heptane. After the loading, the column was eluted sequentially with 1/1 ethyl acetate/heptane (400 mL), ethyl acetate (1200 mL), and then 2% methanol/ethyl acetate (1600) under pressure. The flow rate was 40–50 ml/min. Two hundred mL fractions (except for the 2% methanol/ethyl acetate portion where after the first 200 mL, four 100 mL fractions were collected, and then reverted back to 200 mL) were collected and checked using TLC for the presence of the desired compound.

TLC: Whartman silica gel 60 A (10–12μ) with ethyl acetate as eluent, title compound Rf=0.10, FK-520 Rf=0.35. L-733,725 is visible under UV light and both turns blue after the TLC plate was stained with p-anisaldehyde (mixture of 9.2 mL p-anisaldehyde, 3.75 mL acetic acid, 338 mL, 95% EtOH and 12.5 mL $H_2SO_4$) and heated to >50° C.

Fractions #5–#9 were combined and concentrated in vacuum to a foam, wt. 1.8 g. HPLC showed mostly FK-520.

Fractions #11B (last 100 mL fraction of MeOH/EtOAc eluent) -#15 were combined and concentrated in vacuum to a slightly yellow foam, wt 1.25 g. HPLC showed the title compound to be 94% area pure including the equilibration peak.

HPLC assays. MetaChem ODS-2 4.6×250 mm column at 70° C. UV detector at 210 nm. Flow rate 1.5 ml/min. Eluent A: MeCN, B: 0.01 M phosphate buffer at pH=3.6 with 1% MeCN. Time 0 A/B=60/40, 15 min A/B=70/30, 20 min A/B=80/20, 30 min A/B=80/20. Retention time FK-520 9.9 min, title compound 13.6 min (major) 12.0 min (minor).

This procedure was scaled up to 151 kg silica gel to purify the crude product from the coupling reaction of 640 g imidazole trichloroacetimidate side chain with 2.00 kg FK-520. A total of 876 g of the title compound free base was obtained as amorphous solid (60% yield).

EXAMPLE 2a

Purification of 17-Ethyl-1,14-dihydroxy-12-[2'-(4"-(4'''-(3"",5""-dimethoxyphenyl)-2'''-imidazolylmethyloxy)-3"-methoxycyclohexyl)-1'-methylvinyl]- 23,25-dimethoxy-13, 19,21,27-tetramethyl-11,28-dioxa-4-azatricyclo-[22.3.1.0$^{4,9}$]octacos-18-ene-2,3,10,16-tetraone by HP-20S resin Dry HP-20S resin (32L) was swelled with acetone (40L) for 1h, then loaded onto a chromatography column. The column was eluted with acetone (72L), acetonitrile (72 L), and 50:50 acetonitrile:water (72L). The column was allowed to age with 50:50 acetonitrile:water for 18h. The final volume of resin was 36L.

A crude batch of the title compound free base was divided into two portions of 6.3 kg each. Each portion contained 787 gm of the title compound by HPLC assay. One portion was dissolved in 50:50 $CH_3CN:H_2O$ (90L) and this solution was loaded onto the resin column at a rate of 2 bed volumes per hour. The column eluent was collected in 36L cuts (one bed volume) Once loaded, the column was eluted with 50:50 $CH_3CN:H_2O$ up to fraction 14. The column was then eluted with 60:40 $CH_3CN:H_2O$ from fractions 15–23. Fractions 4–7 contained FK-520 and fractions 14–23 contained the title compound.

(HPLC conditions: YMC ODS-AM column at 50° C., 50:50:0.1 to 80:20:0.1 $CH_3CN:H_2O:H_3PO_4$ in 30 minutes, flow=1.0 ml/min, UV detection at 215 nm.; title compound tR=16.6 min., bis-alkylated impurity tR=19 min., FK-520 tR=24 min.)

Fractions 15–20 were combined and salted by adding solid NaCl (11 kg). After 40 minutes of stirring, the layers were allowed to separate. The lower aqueous layer showed no product by HPLC and was discarded. The upper organic layer (108L) showed 756 gm of free base by HPLC assay. The organic was concentrated in vacuo to afford an oil suspended in about 10 liters of water. The batch was extracted with ethyl acetate (10L) and the organic was passed through a pad of silica gel (1.5 kg). The aqueous was re-extracted with fresh ethyl acetate (2×10L) and each extract was filtered through the pad of silica gel. The filtrate was concentrated in vacuo to afford a foam. The foam was dried under vacuum (29" Hg/25° C.) for 18h. The dry batch weighed 716 gm and was 95% pure by weight. The column recovery was 680 gm (86%).

The column was washed by eluting it with acetone (72L) and acetonitrile (72L) at a rate of 2–3 bed volumes per hour. The column was re-equilibrated with 50:50 acetonitrile: water (72L) and allowed to age 18h.

The second portion of the crude title compound (6.3 Kg at 12.5% purity) was purified as outlined above. The purified batches were combined and dried to afford 1.5 kg of a foam powder. This was 80% pure by weight. The total column recovery was 1.2 kg (75%)

EXAMPLE 3

17-Ethyl-1,14-dihydroxy-12-|2'-(4"-(4'"-(3"", 5""-dimethoxyphenyl)-2'"-imidazolylmethyloxy)-3"-methoxycyclohexyl)-1'-methylvinyl|-23, 25-dimethoxy-13, 19,21,27-tetramethyl-11, 28-dioxa-4-azatricyclo-|22.3.1.0$^{4,9}$|octacos-18-ene-2,3,10 16-tetraone L-tartrate To a 22L three-neck flask equipped with a mechanical stirrer and an addition funnel was charged through a sinter glass filter with the solution of the title compound free base (785 g, 0.779 mol) in ethyl acetate (2.9 L). Additional 5.0 L ethyl acetate was used for rinse. While the solution in the flask was stirred, a solution of L-tartaric acid (116.9 g, 0.779 mol) in water (93.5 mL) was charged with additional 2×2 mL water for rinse. The mixture in the flask became cloudy immediately and 5 g of the title compound tartrate salt seed was added. The mixture was stirred at room temperature overnight. The solid was collected by filtration and washed with 4×500 mL ethyl acetate. It was dried first with sweeping air and then under vacuum at 50° C. with a nitrogen sweep to a weight of 747 g (83% for crystallization step, 51% overall from the imidazole side chain) as a white crystalline solid. m.p.=165.5° C. |α|$_{365}$=607 deg (25° C., 1.0% in MeOH) $^{13}$C NMR (100.61 MHz, acetone-d$_6$-major rotamer) δ211.9, 198.0, 173.3, 169.9, 166.2, 162.1, 147.7, 139.4, 138.9, 136.6, 133.1, 132.2, 124.7, 115.9, 103.4, 99.5, 98.1, 84.0, 82.5, 79.7, 76.2, 74.4, 73.6, 72.9, 70.3, 65.6, 57.4, 57.3, 57.2, 56.4, 55.5$_9$, 55.5$_8$, 49.8, 46.6, 41.1, 39.6, 36.9, 35.5, 35.4, 34.2, 33.4, 31.3, 30.7, 28.5, 26.9, 25.3, 25.2, 21.9, 20.2, 16.6, 16.0, 13.6, 11.9, 10.3. 1H NMR (400.13 MHz, acetone-d$_6$-selected data-major rotamer)δ7.50 (s, 1H), 6.97 (d, J=2.3, 2H), 6.35 (t, J=2.3, 1H), 5.25 (d, J=4.8, 1H), 5.21 (br d, J=9.1, 1H), 4.95 (br d, J=10.3, 1H), 4.77 (s, 2H), 4.63 (br t, J=3.6, 1H), 4.54 (s, 2H), 4.34 (br d, J=13.1, 1H), 3.97 (m, 1H), 3.80 (s, 6H), 3.71 (dd, J=9.5, 1.2, 1H), 3.63 (m, 1H), 3.45 (s, 3H), 3.37 (s, 3H), 3.32 (s, 3H), 2.95 (td, J=13.1 3.2, 1H), 2.79 (dd, J=14.3, 5.6, 1H), 1.68 (d, J=1.2, 3H), 1.62 (d, J=1.2, 3H), 0.94 (d, J=6.3, 3H), 0.92 (d, J=7.1, 3H), 0.90 (d, J=6.7, 3H), 0.82 (t, J=7.5, 3H)

Analysis Calcd. for C$_{59}$H$_{87}$N$_3$O$_{20}$ C 61.10, H 7.50, N 3.60 Found C 60.85, H 7.66, N 3.63

EXAMPLE 3a

Alternative Procedure for the Preparation Of 17-Ethyl-1, 14-dihydroxy-12-|2'-(4"-(4'"-(3"",5""-dimethoxyphenyl)-2'"-imidazolylmethyloxy)-3"-methoxycyclohexyl)-1'-methylvinyl|-23,25-dimethoxy-13,19,21,27-tetramethyl-11, 28-dioxa-4-azatricyclo-|22.3.1.0$^{4,9}$|octacos-18-ene-2,3,10, 16-tetraone L-tartrate In a 50L flask containing 17-ethyl-1,14-dihydroxy-12-|2'-(4"-(4'"-(3"",5""-dimethoxyphenyl)-2'"-imidazolylmethyloxy)-3"-methoxycyclohexyl)-1'-methylvinyl|-23,25-dimethoxy-13,19,21,27-tetramethyl-11, 28-dioxa-4-azatricyclo-|22.3.1.0$^{4,9}$|octacos-18-ene-2,3,10, 16-tetraone free base (1.45 kg at 80% purity, 1.16 kg) was added acetonitrile (7 liters; kf=15 mcg/ml), ethyl acetate (6.5 liters Kf=50 mcg/ml) and water (140 ml) to form a 1% aqueous solution. To the batch was added L-tartaric acid (215 gm). The mixture in the flask became cloudy within 10 minutes, and the tartaric acid dissolved within 1 hour. The batch was seeded with 4 g of the title tartrate salt. The mixture was stirred at room temperature, under N$_2$ for 18h. A sample of the mother liquors showed 12.3 mg/ml of product. The thick white slurry was collected by filtration and washed with pure ethyl acetate (2×1 L). It was dried first with sweeping air and then in vacuum oven on glass trays at 50° C. with a nitrogen sweep for 8 hours. This afforded 1.26 kg of a white solid which was 99.5% pure by weight (94% recovery). The mother liquors contained 121g (9%) of the product.

EXAMPLE 4

The coupling procedure of Example 1 was repeated using a 1:1 molar ratio of the imidazole trichloroacetimidate side chain and FK-520 as provided below.

To a 100 mL three-neck flask charged with imidazole trichloroacetimidate side chain (Kf=1000 mcg/g, 2.00 g, 4.46 mmol) and equipped with a temperature probe, a stirrer and a nitrogen inlet was added FK-520 (3.53 g, 4.46 mmol), 22 mL acetonitrile, 22 mL N,N-dimethyl pivalamide under nitrogen. After all of the solids were dissolved, the reaction mixture was cooled to −25° C. The tetrafluoroboric acid etherate (85%, 0.90 mL, 5.5 mmol) was charged via syringe. The reaction mixture was allowed to warm to −10° C. over two hours. Then 33 mL water was added and the mixture was heated to 50° C. for 24 hours.

The mixture was cooled to room temperature and transferred to a separation funnel and mixed with 88 mL ethyl acetate, 34 mL saturated sodium bicarbonate. The two layers were separated and the aqueous layer was extracted with 22 mL ethyl acetate. The combined organic layer was concentrated in vacuum to a minimum volume and flushed with 10 mL acetonitrile. The residue was transferred to a separation funnel, mixed with 16 L acetonitrile and extracted with 4×220 L hexanes. The desired compound of Example 1 stayed in the bottom acetonitrile layer. The acetonitrile layer was concentrated in vacuum to a minimum volume and flushed with 10 mL ethyl acetate to a thick brown oil. wt 8.28 g. HPLC indicated 2.16 g of the title compound. Other compounds in the mixture includes FK-520 and other side products. The crude product mixture can be purified according to the procedure in Example 2 and converted into the tartrate salt as described in Example 3.

21

EXAMPLE 5

Pharmaceutical Dosage Forms

Crystalline L-tartrate of 17-ethyl-1,14-dihydroxy-12-[2'-(4"-(4'"-(3"",5""-dimethoxyphenyl)-2'"-imidazolylmethyloxy)-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone was used to prepare the following pharmaceutical formulations in accordance with conventional pharmaceutical practices.

A. Soft Gelatin Capsules

Soft gelatin capsules having the following compositions, and containing either 1.5 mg or 10 mg of the active ingredient each were prepared.

| Ingredients | 1.5 mg capsule mg/capsule | 10 mg capsule mg/capsule |
| --- | --- | --- |
| Compd. of Ex. 3* | 1.72 | 11.49 |
| Polyethylene glycol 400 Low aldehyde NF | 585.395 | 575.625 |
| Ethanol 200 proof USP | 67.5 | 67.5 |
| Polysorbate 80 NF | 20.25 | 20.25 |
| Butylated hydroxyanisole (BHA) NF | 0.135 | 0.135 |
| TOTAL | 675.0 | 675.0 |

*Conversion factor tartrate salt/free base = 1.149

B. Hard Gelatin Capsule.

Mannitol DC 300 was spray-coated with an aqueous solution of the compound of Example 3 in sodium lauryl sulfate containing sodium citrate, citric acid and disodium edeate. Stearic acid was used as a lubricant. The resultant admixture was used to fill hard gelatin capsules each having the composition indicated below.

| Ingredients | 5 mg capsule mg/capsule | 30 mg capsule mg/capsule |
| --- | --- | --- |
| Compd. of Ex. 3* | 5.745 | 34.47 |
| Sodium Lauryl Sulfate | 90.0 | 90.0 |
| Sodium Citrate Dihydrate | 1.49 | 4.06 |
| Citric Acid Anhydrous | 0.95 | 0.23 |
| Mannitol DC 300 | 394.32 | 363.74 |
| Disodium Edeate | 2.5 | 2.5 |
| Stearic acid | 5.0 | 5.0 |
| TOTAL | 500 | 500 |

*Conversion factor tartrate salt/free base = 1.149

What is claimed is:

1. A process for the preparation of the compound of formula I:

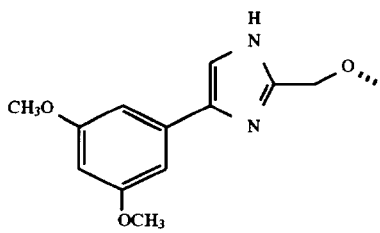

22

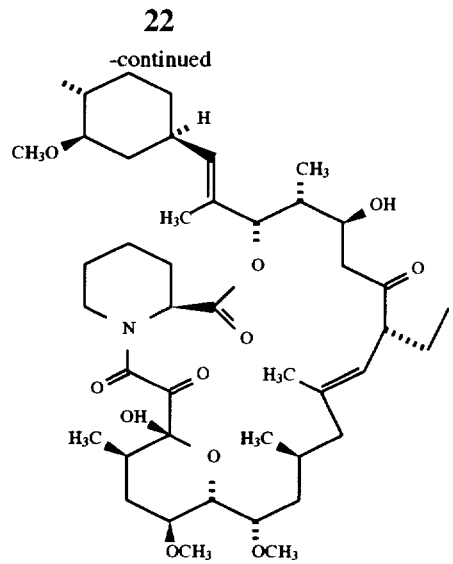

which comprises (1) reacting the compound of formula II:

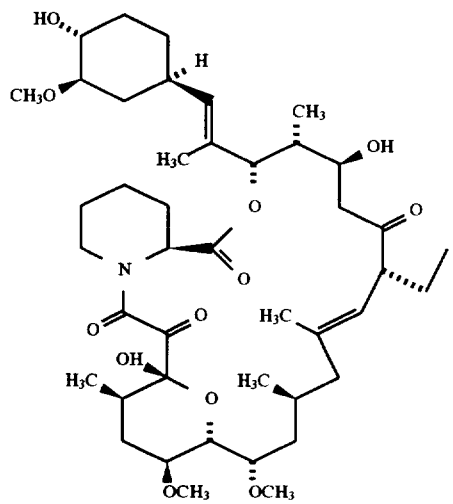

with a compound of formula III:

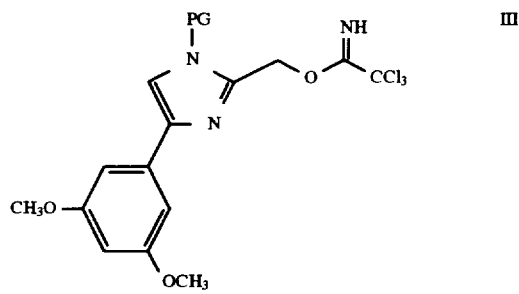

in an inert organic solvent comprising acetonitrile, and an amide of the formula R$^1$CONR$^2$R$^3$ or a carbamate of the formula R$^1$OCONR$^2$R$^3$, and in the presence of an acid; wherein PG is an imidazole protecting group, R$^1$, R$^2$ and R$^3$ are independently C$_{1-7}$ alkyl or R$^1$ and R$^2$ together form —(CH$_2$)$_{2-3}$—; and (2) removing the imidazole protecting group.

2. A process of claim 1 wherein the acid is selected from tetrafluoroboric acid and trifluoromethanesulfonic acid.

3. A process of claim 1 wherein PG is selected from tetrahydropyranyl, tetrahydrofuranyl and 2-methyltetrahydrofuranyl.

4. A process of claim 1 wherein the solvent comprises acetonitrile and N,N-dimethylpivalamide.

5. A process of claim 1 which further comprises treating the compound of formula I with L-tartaric acid to provide the tartrate salt.

6. A process of claim 1 wherein said solvent comprises acetonitrile and N,N-dimethylpivalamide, said acid is tetrafluoroboric acid; and PG is tetrahydrofuranyl.

7. A process of claim 6 which further comprises treating the compound of formula I with L-tartaric acid to provide the tartrate salt.

* * * * *